United States Patent
Claren et al.

(10) Patent No.: US 7,347,813 B2
(45) Date of Patent: Mar. 25, 2008

(54) SURGICAL INSTRUMENT FOR TREATING FEMALE URINARY INCONTINENCE

(75) Inventors: Jan Claren, Lund (SE); Ulf Ulmsten, Danderyd (SE)

(73) Assignee: Ethicon, Inc., Somerville, NJ (US)

( * ) Notice: Subject to any disclaimer, the term of this patent is extended or adjusted under 35 U.S.C. 154(b) by 375 days.

(21) Appl. No.: 11/049,507

(22) Filed: Feb. 2, 2005

(65) Prior Publication Data
US 2005/0148813 A1 Jul. 7, 2005

Related U.S. Application Data (63) Continuation of application No. 10/179,364, filed on Jun. 25, 2002, which is a continuation of application No. 09/051,311, filed as application No. PCT/SE96/012969 on Oct. 8, 1996, now Pat. No. 6,491,703.

(30) Foreign Application Priority Data
Oct. 9, 1995 (SE) .................................. 9503512

(51) Int. Cl.
*A61F 2/02* (2006.01)
(52) U.S. Cl. ........................................ 600/30
(58) Field of Classification Search ........ 128/897–899; 600/29–37; 606/37, 72, 119, 139, 141, 144–146, 606/148, 151, 167, 185, 222–225, 232; 604/263, 604/273–274
See application file for complete search history.

(56) References Cited

U.S. PATENT DOCUMENTS 2,993,589 A 7/1961 Zoller et al.
3,038,475 A 6/1962 Orcutt
3,212,502 A 10/1965 Myers
4,392,495 A 7/1983 Bayers (Continued)

FOREIGN PATENT DOCUMENTS

AU 278089 6/1965

(Continued)

OTHER PUBLICATIONS

Petros, "An Integral Theory of Female Urinary Incontinence", *Acta Obstetricia et Gynecologica Scandinavica* vol. 69, Supplemental 153 (1990) pp. 43-51, Almqvist & Wiksell Intl., Sweden.

(Continued)

*Primary Examiner*—Charles A. Marmor, II
*Assistant Examiner*—Christine D. Hopkins (57) ABSTRACT

A surgical assembly and method for treating female urinary incontinence. The assembly includes a substantially flat, flexible tape having first and second ends, wherein at least a portion of the tape is adapted to be permanently implanted into a female patient's body as a loop beneath the urethra. The assembly further includes a flexible sheath having a first portion covering a first length of the tape and a second portion covering a second length of the tape. The first and second portions substantially cover the entire length of the implant portion of the tape prior to implantation of the tape and sheath combination into the patient's body. Following implantation into the patient's body, the first and second portions of the sheath are removable from the first and second ends of the tape respectively.

5 Claims, 5 Drawing Sheets

U.S. PATENT DOCUMENTS

| | | | |
|---|---|---|---|
| 4,455,690 A | 6/1984 | Homsy | |
| 4,668,233 A | 5/1987 | Seedhom et al. | |
| 4,705,281 A | 11/1987 | Spinas | |
| 4,775,380 A * | 10/1988 | Seedhom et al. | 623/13.16 |
| 5,019,032 A | 5/1991 | Robertson | |
| 5,122,155 A | 6/1992 | Eberbach | |
| 5,149,329 A | 9/1992 | Richardson | |
| 5,168,262 A | 12/1992 | Okayama | |
| 5,180,385 A | 1/1993 | Sontag | |
| 5,382,257 A | 1/1995 | Lewis et al. | |
| 5,549,619 A * | 8/1996 | Peters et al. | 606/151 |
| 5,671,695 A | 9/1997 | Schroeder | |
| 5,871,536 A | 2/1999 | Lazarus | |
| 5,954,057 A | 9/1999 | Li | |
| 6,273,852 B1 | 8/2001 | Lehe et al. | |
| 2003/0004395 A1 | 1/2003 | Therin | |

FOREIGN PATENT DOCUMENTS

| | | |
|---|---|---|
| AU | 441561 | 1/1972 |
| DE | 4334419 A | 4/1995 |
| EP | 153831 A | 9/1985 |
| EP | 223370 A | 5/1987 |
| EP | 597446 A | 11/1993 |
| EP | 598976 | 6/1994 |
| EP | 0 852 930 A | 7/1998 |
| EP | 1151722 A | 11/2001 |
| SE | 503271 C | 4/1996 |
| WO | WO 86/07275 A | 12/1986 |
| WO | WO 90/03766 A | 4/1990 |
| WO | WO 90/06567 A | 6/1990 |
| WO | WO 94/05213 A | 3/1994 |
| WO | WO 95/13033 A | 5/1995 |
| WO | WO 96/06567 A1 | 3/1996 |
| WO | WO 97/13465 A | 4/1997 |
| WO | WO 00/74613 A | 12/2000 |

OTHER PUBLICATIONS

Petros., "Ambulatory Surgery for Urinary Incontinence and Vaginal Prolapse", *The Medical Journal of Australia*, vol. 161 (Jul. 18, 1994) pp. 171-172.

Petros, "An Integral Theory and its Method for the Diagnosis and Management of Female Urinary Incontinence", *Scandinavian Journal of Urology and Nephrology*, vol. 69, Supplement No. 153 (1993) pp. 77-79.

Kersey, "The Gauze Hammock Sling Operation in the Treatment of Stress Incontinence", *British Journal of Obstetrics and Gynaecology*, vol. 90 (Oct. 1983) pp. 945-949.

Ulmsten et al., "Intravaginal Slingplasty", *Zentralblatt fur Gynakologie*, vol. 116 (1994) pp. 398-404.

Ulmsten et al., "An Ambulatory Surgical Procedure Under Local Anesthesia for Treatment of Femal Urinary Incontinence", *International Urogynecology Journal*, vol. 7 (1996) pp. 81-86.

Medcompare; Mersilene Polyester Fiber Mesh, a printout (one page) from the following website http://www.medcompare.com/itemdetails.asp?itemid=35861, Apr. 2005.

Brenner, "Mesh Material in Hernia Repair", Expert Meeting on Hernia Surgery (1994) pp. 178-179, a printout (one page) from the following website http://www.herniasolutions.com/professional/clin.html.

Petros P., The Female Pelvic Floor Function, Dysfunction and Management According to the Integral Theory by P. Petros 2004, Second Edition 2006.

* cited by examiner

SURGICAL INSTRUMENT FOR TREATING FEMALE URINARY INCONTINENCE

CROSS-REFERENCE TO RELATED APPLICATIONS

This application is a continuation application of U.S. application Ser. No. 10/179,364, filed Jun. 25, 2002, which is a continuation application of U.S. application Ser. No. 09/051,311, Jul. 27, 1998, now U.S. Pat. No. 6,491,703, which was the National Stage of International Application No. PCT/SE96/01269, filed Oct. 8, 1996.

FIELD OF THE INVENTION

The present invention relates to a surgical instrument and a method for treating female urinary incontinence.

BACKGROUND OF THE INVENTION

Document WO-A-9606567 discloses a surgical instrument and method for treating urinary incontinence that involves permanently implanting a tape as a loop beneath the patient's urethra, where the ends of the tape extend up to the abdominal wall on either side of the urethra.

BRIEF SUMMARY OF THE INVENTION

The present invention provides an improved device for treating urinary incontinence. A surgical assembly for treating female urinary incontinence is provided including a substantially flat, flexible tape having first and second ends. At least a portion of the tape is adapted to be permanently implanted into a female patient's body as a loop beneath the urethra. The assembly further includes a flexible sheath having a first portion covering a first length of the tape and a second portion covering a second length of the tape. The first and second portions substantially cover the entire length of the implant portion of the tape prior to implantation of the tape and sheath combination into the patient's body. Following implantation into the patient's body, the first and second portions of the sheath are removable from first and second ends of the tape respectively.

According to one embodiment, the first and second portions of the sheath are coupled to one another prior to implantation. The sheath may further include first and second portions, wherein the first and second portions are joined at a perforation line positioned substantially at a longitudinal center.

A method is also provided for treating female urinary incontinence that includes providing a surgical assembly including a substantially flat, flexible tape having first and second ends, wherein least a portion of the tape is adapted to be permanently implanted into a female patient's body as a loop beneath the urethra, and a flexible sheath having a first portion covering a first length of the tape and a second portion covering a second length of the tape. The first and second portions substantially cover at least the implant portion of the tape prior to implantation. The method further includes implanting the tape and sheath as a loop beneath the urethra, separating the first and second portions of the sheath, removing the first portion of the sheath from the patient via the first end of the tape, removing the second portion of the sheath from the patient via the second end of the tape, and leaving the tape implanted within the patient.

According to one embodiment, the first and second sheath portions are joined with one another prior to implantation, and the separating step further includes physically severing the first and second sheath portions from one another. The severing step may further include severing the first sheath portion from the second sheath portion along a perforation line in the sheath. According to one embodiment, the perforation line is substantially at a longitudinal center of the sheath.

Also provided is a surgical assembly for treating female urinary incontinence including a substantially flat, flexible tape having first and second ends and an implant portion therebetween adapted to be implanted into a female patient's body as a loop beneath the urethra. Also included is a flexible sheath having a first portion covering a first length of the tape and a second portion covering a second length of the tape. The first and second portions substantially cover the entire length of the implant portion of the tape prior to implantation of the tape and sheath combination into the patient's body. The tape and sheath are not fixedly secured to one another along the implant portion of the tape.

In one embodiment, the tape and sheath are fixedly secured to one another at a location other than along the implant portion of the tape. In yet another embodiment, the first and second sheath portions are affixed to one another prior to implantation, but are removable from the first and second ends of the tape respectively following implantation when severed from one another substantially at a longitudinal center thereof.

BRIEF DESCRIPTION OF THE DRAWINGS

The invention will be explained in more detail with reference to the accompanying drawings which disclose embodiments of the surgical instrument according to the invention.

DETAILED DESCRIPTION

In the following description, the same reference numerals have been used for corresponding details of the instrument as in WO-A-9606567, which is incorporated herein by reference in its entirety.

An exemplary surgical instrument for implanting a tape according to the present invention includes a cylindrical tubular shank 10 having at one end thereof a handle 11. At the other end of the shank there is a socket 14. A cylindrical shaft 15 is rotatably mounted in the shank and can be rotated manually by means of a knob 16 mounted to one end of the shaft. The other end of the shaft forms a cylindrical portion 17 of smaller outside diameter than the shaft, which joins a portion 18 having external threads and a smooth end portion 19 forming a guide pin at the other end of the shaft. Portions 18 and 19 are received in the portion of socket 14 projecting from the shank. The surgical instrument as described so far is in agreement with the instrument disclosed in WO-A-

Figure 1:
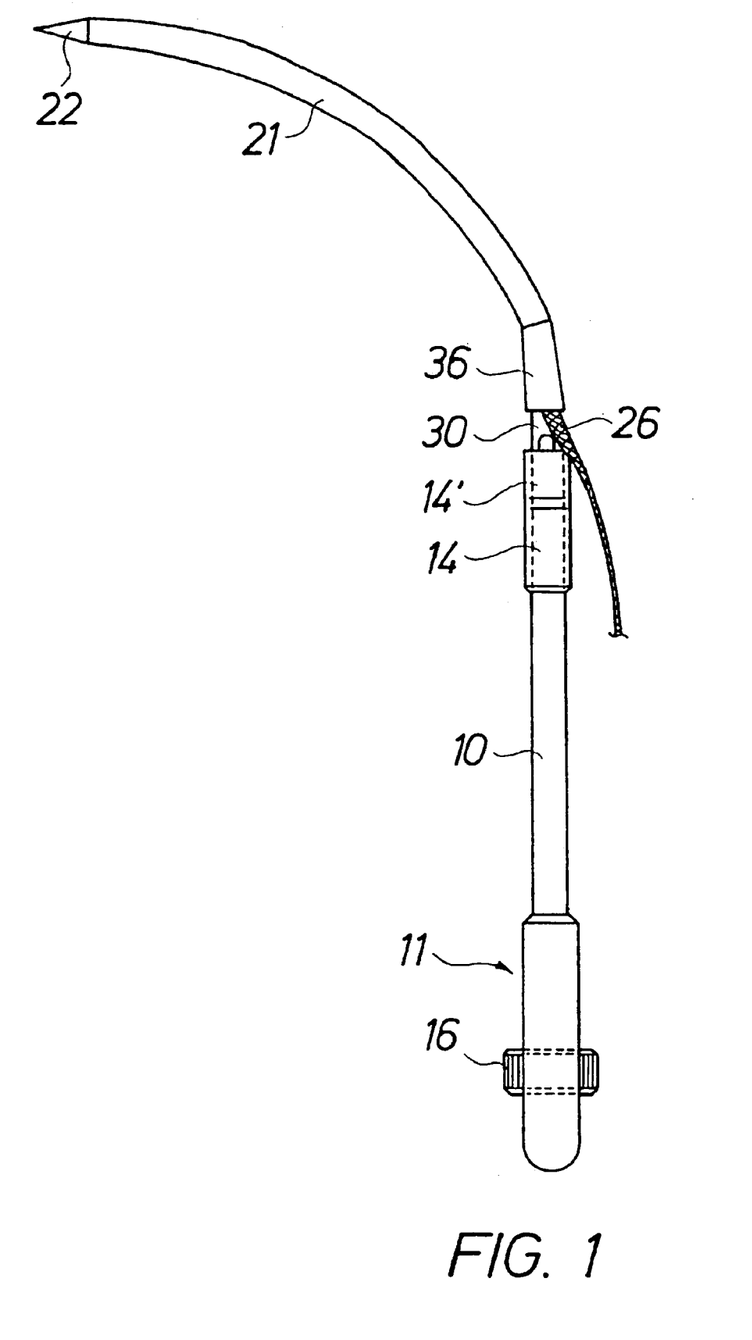
FIG. 1 is a side view of one surgical instrument that can be used to implant the surgical assembly of the present invention.

9606567 except that the end portion 14' of socket 14 is flattened from opposite sides (FIGS. 1 and 2) so that the cross section of the end portion is non-circular.

The surgical instrument also includes an exchangeable and disposable needle 21, which at one end is attached to the shank and extends over substantially a quarter of a circle to the other free end in order to follow substantially the profile of the pubis between the vagina and the abdominal wall. The needle has uniform circular cross section and has a smooth, preferably polished outside surface. At the free end, the needle forms a point 22 by terminating in a conical portion.

For attachment of needle 21 to shank 10, the needle includes a straight portion 30 which is cylindrical but has milled flat faces 31 extending from the adjacent end of the needle which is to be received by socket portion 14'. The needle should be oriented in a predetermined rotational position in relation to the shank, and more particularly it should project at right angles to the plane of handle 11. This rotational position is secured by the non-circular shape of socket portion 14', and the end portion of the needle having the flat faces 31 that fit into socket portion 14'. The end portion of the needle having the flat faces 31 joins the body of the needle over a conical portion 32, which tapers towards shoulder 33.

An axial blind hole extends from the end surface of the needle and has a threaded portion 23 and inwardly thereof, a narrower, cylindrical portion 24. Guide pin 19 is dimensioned to be guidingly received by the latter portion when the threaded portion 18 is screwed into threaded portion 23 of the blind hole by rotating shaft 15 by manual rotation of knob 16 with the end surfaces of the shank and the needle being pressed against each other. This attachment also is in agreement with that described in WO-A-9606567.

Figure 2:
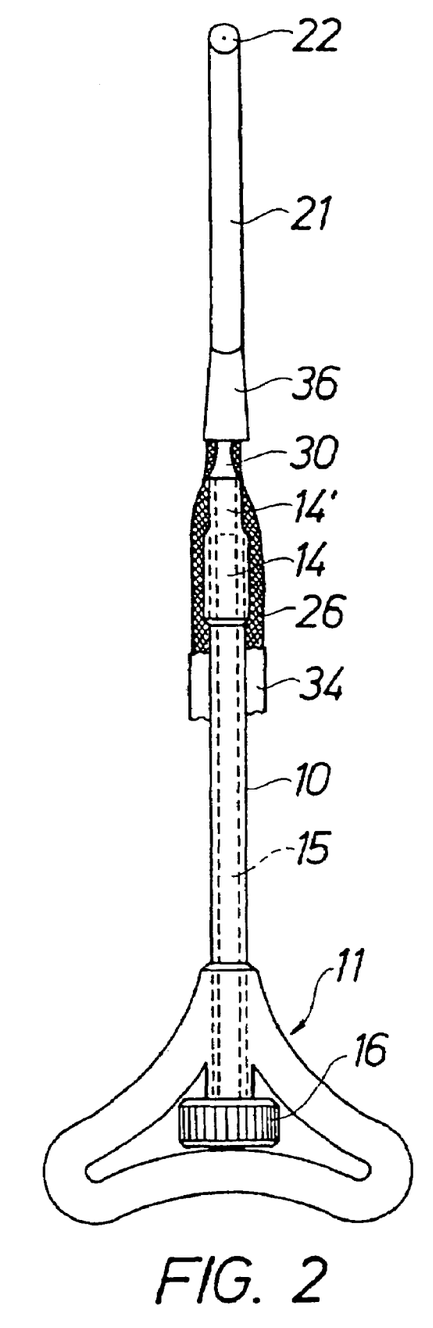
FIG. 2 is a plan view of the surgical instrument of FIG. 1.
Figure 3:
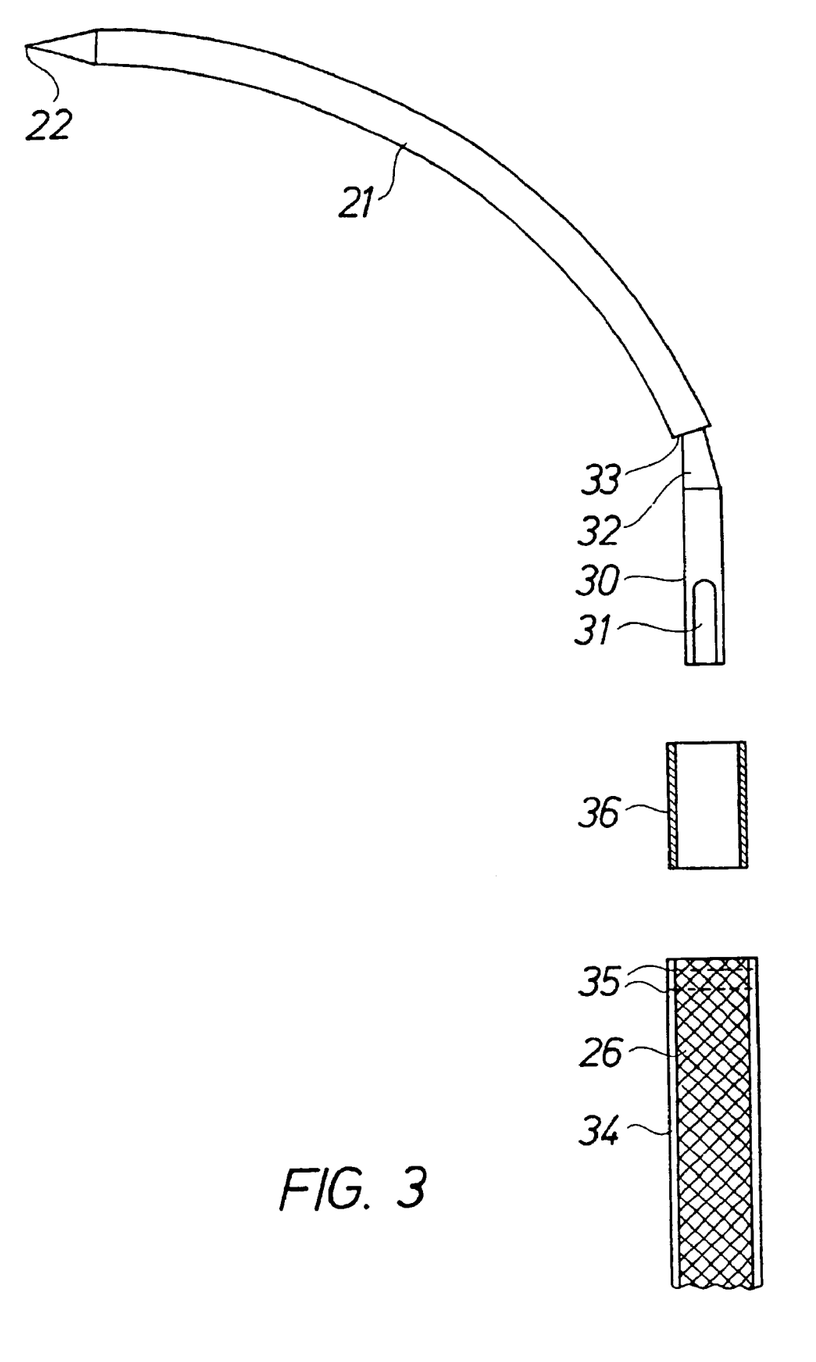
FIG. 3 is an enlarged fragmentary axial cross sectional view the instrument of FIG. 1 illustrating attachment to a tape and sheath combination according to one embodiment of the present invention.
Figure 4:
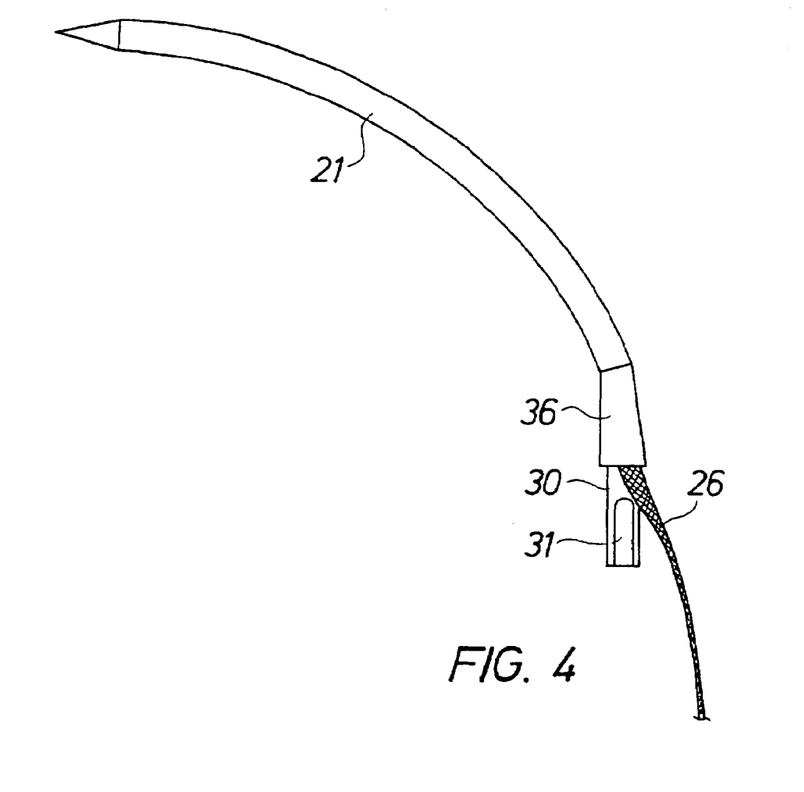
FIGS. 4 and 5 illustrate various features or components of the instrument of FIG. 1.
Figure 5:
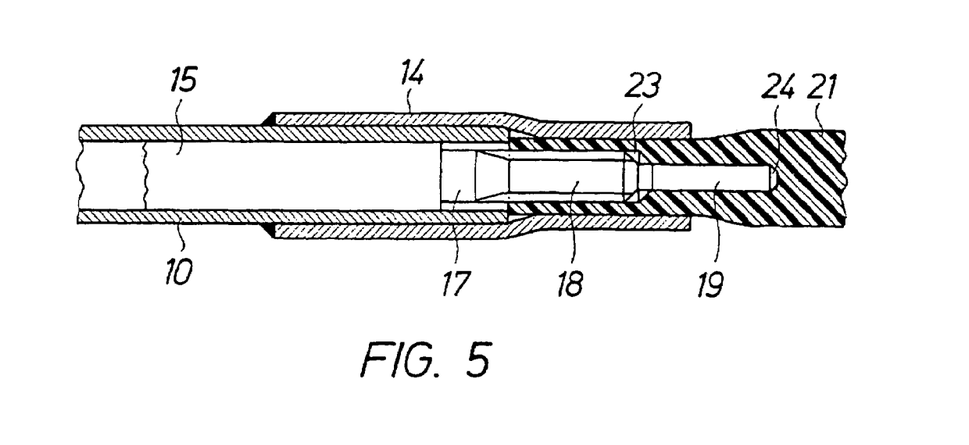

When the method as described in WO-A-9606567 is practiced, two needles 21A and 21B of the embodiment described are connected one at each end of a tape 26. According to the present invention, the tape of the preferred embodiment comprises a mesh or netting forming openings of the order of 1 mm. A suitable material for the tape is PROLENE®, a knitted polypropylene mesh having a thickness of about 0.7 mm and manufactured by Ethicon, Inc. of Somerville, N.J. This material is approved by the FDA in the U.S.A. for implantation into the human body. The netting (tape) preferably has a width of approximately 10 mm and is enclosed in a thin polyethylene sheath 34, which in flattened condition has substantially the same width as the tape, although a difference in width is shown in FIG. 2 in order to make the provision of the sheath more clear. The length of the netting should be approximately 400 mm. The netting and the sheath may be interconnected by means of two rows 35 of stitching. The end portion of the sheath may be attached to the conical portion 32 of the needle by means of a suitable strong glue, and the interconnection of the needle and sheath is covered by a rubber shrink hose 36 that extends from the shoulder 33 over the conical portion 32 and partly over the cylindrical end portion 30 of the needle. The shrink hose is substantially flush with the surface of the needle at the shoulder. By this arrangement, the netting is securely attached to the needle for implantation of the combination, although various other means by which to substantially prevent movement of the sheath relative to the tape during implantation will be apparent to those skilled in the art.

The purpose of sheath 34 is above all to facilitate the insertion of the netting in the manner described in WO-A-9606567. In other words, as the netting is being inserted to form a urethral sling, i.e., by extending the ends thereof from the vaginal wall to the abdominal skin, the sheath prevents the edges of the netting from irritating or damaging the surrounding body tissues.

Once the tape has been properly placed, the sheath must be removable from the tape to enable ingrowth into the tape to thereby secure the tape in place. One manner in which to accomplish this is to physically separate the sheath substantially at the longitudinal center thereof (or at least the portion of the sheath in the vicinity of the vaginal incision), and to withdraw the two halves of the sheath from the netting by pulling at the respective outer ends (the ends extending outwardly from the abdominal incisions). This may be facilitated by incorporating into the sheath a perforation substantially at the longitudinal center thereof as indicated by the dot-and-dash line 37 in FIG. 6. It may, however, also be accomplished by any other suitable means that will allow first and second portions of the tape to be removed from first and second ends of the tape respectively.

Figure 6:
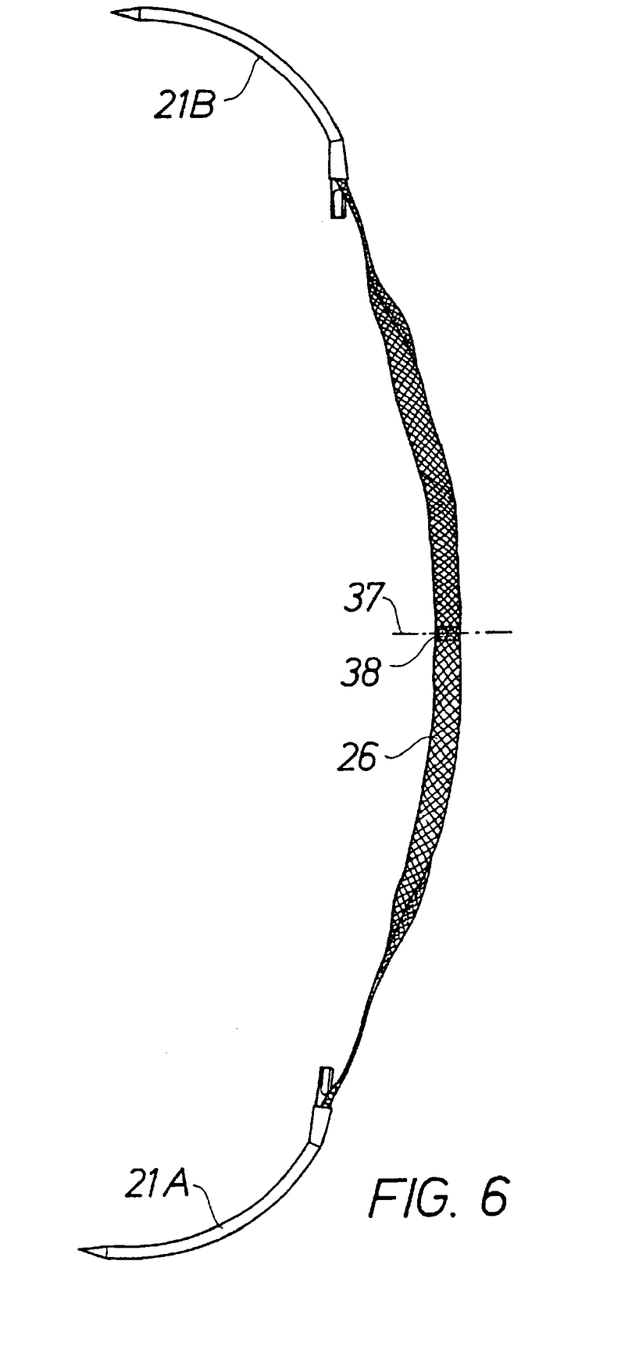
FIG. 6 illustrates the surgical needles of FIG. 1 in conjunction with a tape and sheath combination according to one embodiment of the present invention.

As an additional feature, the longitudinal center of the sheath could be indicated by a visible color mark 38, FIG. 6, so that the surgeon readily can see when the netting is symmetrically located with reference to the urethra during the surgery.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention, which is limited only by the claims set forth below.

What is claimed is:

1. A surgical assembly for treating female urinary incontinence, comprising:

a substantially flat, flexible tape having first and second ends, wherein at least a portion of the tape is adapted to be permanently implanted into a female patient's body as a loop beneath an urethra;

a flexible sheath having a first portion covering a first length of the tape and a second portion covering a second length of the tape, the first and second portions substantially covering an entire length of the implant portion of the tape prior to implantation of the tape and sheath combination into the patient's body and being coupled to one another prior to implantation, at a perforation line positioned substantially at a longitudinal center of the sheath, wherein, following implantation into the patient's body, the first and second portions of the sheath are removable from first and second ends of the tape respectively.

2. A method for treating female urinary incontinence, comprising:

providing a surgical assembly including a substantially flat, flexible tape having first and second ends wherein least a portion of the tape is adapted to be permanently implanted into a female patient's body as a loop beneath an urethra, and a flexible sheath having a first portion covering a first length of the tape and a second portion covering a second length of the tape, wherein the first and second portions substantially cover at least the implant portion of the tape prior to implantation;

implanting the tape and sheath as a loop beneath the urethra;

separating the first and second portions of the sheath;

removing the first portion of the sheath from the patient via the first end of the tape;

removing the second portion of the sheath from the patient via the second end of the tape; and leaving the tape implanted within the patient.

3. The method according to claim 2, wherein the first and second sheath portions are joined to one another prior to implantation, and the separating step further comprises severing the first and second sheath portions from one another.

4. The method according to claim 3, wherein the severing step further comprises severing the first sheath portion from the second sheath portion along a perforation line in the sheath.

5. The method according to claim 4, wherein the perforation line is substantially at a longitudinal center of the sheath.

* * * * *

UNITED STATES PATENT AND TRADEMARK OFFICE
Certificate

Patent No. 7,347,813 B2                                                          Patented: March 25, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Ulf Ulmsten, Danderyd (SE).

Signed and Sealed this Ninth Day of August 2011.

MIRANDA LEE
*Supervisory Patent Examiner*
Art Unit 3735
Technology Center 3700